United States Patent
Chan et al.

(10) Patent No.: US 10,610,085 B2
(45) Date of Patent: Apr. 7, 2020

(54) OPTICAL SENSING-ENABLED INTERVENTIONAL INSTRUMENTS FOR RAPID DISTRIBUTED MEASUREMENTS OF BIOPHYSICAL PARAMETERS

(75) Inventors: Raymond Chan, San Diego, CA (US); Maya Ella Barley, Eindhoven (NL); Adrien Emmanuel Desjardins, Eindhoven (NL); Guy Shechter, Briarcliff Manor, NY (US); Gert 'T Hooft, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 892 days.

(21) Appl. No.: 13/501,101

(22) PCT Filed: Aug. 26, 2010

(86) PCT No.: PCT/IB2010/053845
§ 371 (c)(1),
(2), (4) Date: Apr. 10, 2012

(87) PCT Pub. No.: WO2011/048509
PCT Pub. Date: Apr. 28, 2011

(65) Prior Publication Data
US 2012/0197097 A1 Aug. 2, 2012

Related U.S. Application Data

(60) Provisional application No. 61/254,317, filed on Oct. 23, 2009.

(51) Int. Cl.
*A61B 1/00* (2006.01)
*A61B 1/005* (2006.01)
(Continued)

(52) U.S. Cl.
CPC .......... *A61B 1/00165* (2013.01); *A61B 1/005* (2013.01); *A61B 90/06* (2016.02);
(Continued)

(58) Field of Classification Search
CPC ....... A61B 19/5244; A61B 19/46; A61B 5/06; A61B 2019/5261; A61B 2019/5251;
(Continued)

(56) References Cited

U.S. PATENT DOCUMENTS

| 5,124,130 A | 6/1992 | Costello et al. |
| 5,195,963 A | 3/1993 | Yafuso et al. |

(Continued)

FOREIGN PATENT DOCUMENTS

| CN | 101099657 A | 1/2008 |
| EP | 1319364 | 6/2003 |

(Continued)

OTHER PUBLICATIONS

Men et al. "Intelligent multiparameter sensing with fiber Bragg gratings." Appl. Phys. Lett. 93, 071110 (2008). (Year: 2008).*
(Continued)

*Primary Examiner* — Amelie R Davis

(57) ABSTRACT

An interventional instrument, system and method include an elongated flexible member (100) having one or more segmented sections (101) disposed longitudinally. An optical fiber (104) is disposed internally in the flexible member. A plurality of optical sensors (102) are coupled to the optical fiber and distributed along a length of the flexible member such that the optical sensors are positioned to monitor parameters simultaneously at different positions or at different data sources along the flexible member to provide distributed sensing.

28 Claims, 5 Drawing Sheets

(51) Int. Cl.
*A61B 90/00* (2016.01)
*A61B 34/20* (2016.01)
*A61B 17/00* (2006.01)

(52) U.S. Cl.
CPC ..... *A61B 34/20* (2016.02); *A61B 2017/00022* (2013.01); *A61B 2034/2061* (2016.02)

(58) Field of Classification Search
CPC ..... A61B 1/00165; A61B 90/06; A61B 1/005; A61B 2034/2061; A61B 34/20; A61B 2017/00022
See application file for complete search history.

(56) References Cited

U.S. PATENT DOCUMENTS

| | | | |
|---|---|---|---|
| 5,397,411 | A | 3/1995 | Costello et al. |
| 5,493,113 | A | 2/1996 | Dunphy et al. |
| 6,120,457 | A * | 9/2000 | Coombes ........... A61B 5/02156 600/486 |
| 6,256,090 | B1 | 7/2001 | Chen et al. |
| 6,285,806 | B1 | 9/2001 | Kersey et al. |
| 6,315,712 | B1 | 11/2001 | Rovegno |
| 6,471,710 | B1 | 10/2002 | Buchholtz |
| 6,659,957 | B1 * | 12/2003 | Vardi et al. ................. 600/467 |
| 6,748,255 | B2 | 6/2004 | Fuimaono et al. |
| 6,868,195 | B2 | 3/2005 | Fujita |
| 6,869,430 | B2 | 3/2005 | Balbierz et al. |
| 6,898,337 | B2 | 5/2005 | Averett et al. |
| 7,228,017 | B2 | 6/2007 | Xia et al. |
| 7,433,552 | B2 | 10/2008 | Kiesel et al. |
| 7,528,860 | B2 | 5/2009 | Moore |
| 8,306,592 | B2 | 11/2012 | Akio et al. |
| 8,961,436 | B2 | 2/2015 | Leo et al. |
| 9,907,618 | B2 | 3/2018 | Leo et al. |
| 2002/0041723 | A1 * | 4/2002 | Ronnekleiv ........... A61B 5/0084 385/12 |
| 2002/0052546 | A1 | 5/2002 | Frantz et al. |
| 2004/0165810 | A1 | 8/2004 | Fujita |
| 2005/0075555 | A1 | 4/2005 | Glukhovsky et al. |
| 2006/0013523 | A1 | 1/2006 | Childers et al. |
| 2007/0075225 | A1 * | 4/2007 | Xia ...................... G01N 21/7703 250/227.14 |
| 2007/0109778 | A1 | 5/2007 | Chang et al. |
| 2007/0265503 | A1 | 11/2007 | Schlesinger et al. |
| 2008/0255629 | A1 * | 10/2008 | Jenson et al. ................... 607/19 |
| 2009/0076476 | A1 * | 3/2009 | Barbagli et al. ............. 604/500 |
| 2011/0090486 | A1 | 4/2011 | Udd |
| 2011/0172519 | A1 * | 7/2011 | Cao et al. ..................... 600/424 |
| 2013/0012809 | A1 | 1/2013 | Schlesinger et al. |

FOREIGN PATENT DOCUMENTS

| | | |
|---|---|---|
| JP | 7270261 A | 10/1995 |
| JP | 8182665 A | 7/1996 |
| JP | 8182665 A | 7/1996 |
| JP | 3507161 B2 | 3/2004 |
| JP | 2006043449 A | 2/2006 |
| JP | 2007044412 A | 2/2007 |
| JP | 2007322918 A | 12/2007 |
| JP | 2008173397 A | 7/2008 |
| WO | WO199118306 A1 | 11/1991 |
| WO | WO200113060 | 2/2001 |
| WO | 03094723 A1 | 11/2003 |
| WO | WO2009049038 | 4/2009 |

OTHER PUBLICATIONS

Kyuma, K. et al. "Fiber-optic current and voltage sensors using a Bi12GeO20 single crystal," J. Lightwave Technol. LT-1, 93-97 (1983).

Norimatsu, M. et al. "Bi12SiO20 crystal application for voltage sensor in optical fibers," Ferroelectrics 75, 189-196 (1987).

Rose, A.H. et al., "Optical fiber voltage sensors for broad temperature ranges," in Fiber Optic Components and Reliability, P.M. Kopera and D. K. Paul, eds., Proc. SPIE 1580, 95-103 (1992).

Ambrosino, C. et al., "Novel Magnetic Sensor Based on Fiber Bragg Grating and Magnetic Shape Memory Alloys," 1st International Conference on Sensing Technology Nov. 21-23, Palmerston North, New Zealand, 350-354 (2005).

Zhang, L. et al., "On SDM/WDM FBG Sensor Net for Shape Detection of Endoscope", Mechatronics and Automation, 2005 IEEE Intenational Conference Niagara Falls, ON Canada Jul. 29-Aug. 1, 2005, Abstract.

Fernandez, F. et al., "Multi-component force sensor based on multiplexed fibre Bragg grating strain sensors; Multi-component force sensor based on multiplexed FBG strain sensors", Meausrement Science and Technology, Jul. 1, 2001 IOP, Bristol, GB, vol. 12, Nr: 7, p. 810-813.

\* cited by examiner

OPTICAL SENSING-ENABLED INTERVENTIONAL INSTRUMENTS FOR RAPID DISTRIBUTED MEASUREMENTS OF BIOPHYSICAL PARAMETERS

This disclosure relates to medical devices, and more particularly to medical devices employing fiber optic technology for multi-parameter measuring and monitoring.

Interventional instruments typically measure only one physical parameter. Examples include pressure/flow wires for hemodynamic monitoring at a tip location, cardiac mapping electrodes for voltage measurements at discrete electrode locations, and ablation catheters which allow for tissue temperature and impedance measurements at the tip. Spatial tracking via impedance measurement or electromagnetic (EM) sensing can be incorporated into these devices to facilitate navigation; however, tracking measurements are generally localized to the tip and are sensitive to environmental heterogeneity or temporal variation in the underlying impedance/EM characteristics. In addition, tracking coils can be difficult to miniaturize within the submillimeter range while maintaining signal-to-noise and other performance characteristics. Trade-offs between coil size and performance constrain the overall footprint of the instrument and size of a working channel or lumen within the instrument. In addition, during magnetic resonance (MR)-guided electrophysiology (EP) procedures, a discrete point on the catheter may be localized by means of a bulky coil and transformer cable. The coil and cable generally have sizes that preclude their use in tracking multiple points along the catheter body. Furthermore, RF generator noise during ablation impedes the ability to accurately track the coil using MR.

In accordance with the present principles, optical fiber based sensing is employed. The instruments in accordance with the present principles provide immunity to electromagnetic interference and no electromagnetic emissions. Optical sensors are employed which are passive and therefore intrinsically safe. Optical sensors in an array have the ability to be multiplexed. In addition, the possibility of multi-parameter sensing (strain, temperature, pressure, etc.) is provided as well as the possibility of distributed sensing when using optics. The sensors have high sensitivity (down to nanostrains when interferometry is used in optical interrogation), and are insensitive to variation in signal amplitude (e.g., when fiber Bragg sensors are employed with wavelength detection). Fibers are small and light weight, and ideal for minimally invasive applications.

For many medical applications, in particular for those requiring minimally-invasive navigation and instrumentation, fiber optic sensing (of shape and other relevant biomedical parameters) offers the allure of high-accuracy and high-precision localization/physiological parameter sensing at high spatial resolution along the length of the fiber with high temporal resolution. Given the light-weight, elongated form factor of optical fiber and compact cross-sectional footprint, fiber technology may be employed in clinical applications needing fine spatiotemporal tracking of a continuous and elongated medical device/instrument that can be introduced into the body percutaneously or via natural orifices.

In addition, interventional procedures are provided that employ guide wires, catheters, flexible endoscopes (or other similar elongated instruments) in which there is a need for compact and robust multipoint/distributed sensing of physiological motion characteristics and parameters including temperature, pressure, and voltage changes. Fiber-optic Bragg Gratings (FBG) can be incorporated directly into the body of an elongated instrument such as a guide wire or catheter without significantly changing the instrument's mechanical properties or form factor/footprint. Further, rapid multipoint and multi-parameter measurements of segmental motion, voltage, temperature, and pressure are possible with the introduction of coatings or crystal materials (e.g., $Bi_{12}TiO_{20}$ crystals for voltage sensing, Ni—Mn—Ga memory shape metal alloys for magnetic sensing, Zn metal vapor deposition for enhanced temperature sensing, etc).

The incorporation of coated fiber Bragg gratings into guide wires, catheters, or other flexible elongated instruments overcomes limitations of the prior art by allowing for rapid multi-parameter measurements along the instrument. Voltage, magnetic field, temperature (hemodynamic flow can be derived from temperature changes), and pressure are possible with introduction of coatings or crystal materials (e.g., $Bi_{12}TiO_{20}$ crystals for voltage sensing, Ni—Mn—Ga memory shape metal alloys for magnetic sensing, Zn metal vapor deposition for enhanced temperature sensing, etc.). These instruments permit segmental motion tracking in a distributed fashion along the length of the instrument. Different segments are influenced primarily by different physiological motions, e.g., respiratory versus cardiac and therefore, motion-specific compensation or gating of instrument data becomes possible (without the need for additional catheters/devices, e.g., tracking of a coronary sinus catheter, separate from the main EP catheter to obtain respiratory compensation or gating of X-ray fluoroscopy).

The incorporation of coated fiber Bragg gratings into guide wires, catheters, or other flexible elongated instruments overcomes limitations of the prior art by allowing for rapid multi-parameter measurements along the instrument. Simultaneous measurements may be made for motion, voltage, temperature, pressure, etc. in a distributed fashion at the "effector" or other segment of the instrument (e.g., at the distal 10 cm segment including the tip of a loop/lasso mapping catheter used in electrophysiology procedures) using a single (or multiple) sensing fiber(s) and an optical interrogation system (as opposed to multiple separate sensors, cabling, and a significantly larger footprint that are needed to achieve this with conventional electronics).

Mechanical deformation of the "effector" segment of the instrument may be tracked to monitor changes in biological tissue in response to intervention, e.g., measurement of tissue-induced FBG strains in a electrophysiology loop catheter to estimate electromechanical response, or to estimate intervention impact on cardiac contractility.

Optical Frequency Domain Reflectometry (OFDR) may be employed to measure thousands of sensors with the same nominal reflected wavelength with high spatial and temporal resolution. OFDR uses a continuously tunable laser to interrogate a series of FBGs along an optical fiber. Reflected light from these elements is detected interferometrically to estimate the wavelength shift associated with strain in the fiber Bragg elements. Strains from multiple FBGs can be measured and the corresponding fiber shape can be reconstructed from several optical cores running in parallel.

An interventional instrument, system and method include an elongated flexible member having one or more segmented sections disposed longitudinally. An optical fiber is disposed internally in the flexible member. A plurality of optical sensors are coupled to the optical fiber and distributed along a length of the flexible member such that the optical sensors are positioned to monitor separate parameters simultaneously along the flexible member to provide distributed sensing.

A system for an interventional procedure includes an interventional instrument including an elongated flexible member having one or more segmented sections disposed longitudinally. At least one optical fiber is disposed internally in the flexible member, and a plurality of optical sensors are coupled to the at least one optical fiber and distributed along a length of the flexible member such that the optical sensors are positioned to monitor parameters simultaneously at least one of different positions and for different data sources to provide distributed sensing. A workstation is configured to provide an interface to control the interventional instrument and to perform a procedure using the interventional instrument.

A medical interventional method includes providing an interventional instrument including an elongated flexible member having one or more sections disposed longitudinally, at least one optical fiber disposed internally in the flexible member, and a plurality of optical sensors coupled to the at least one optical fiber and distributed along a length of the flexible member such that the optical sensors are positioned to monitor parameters simultaneously at least one of different positions and for different data sources parameters along the flexible member to provide distributed sensing. The interventional instrument is guided into a body to perform a medical procedure.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
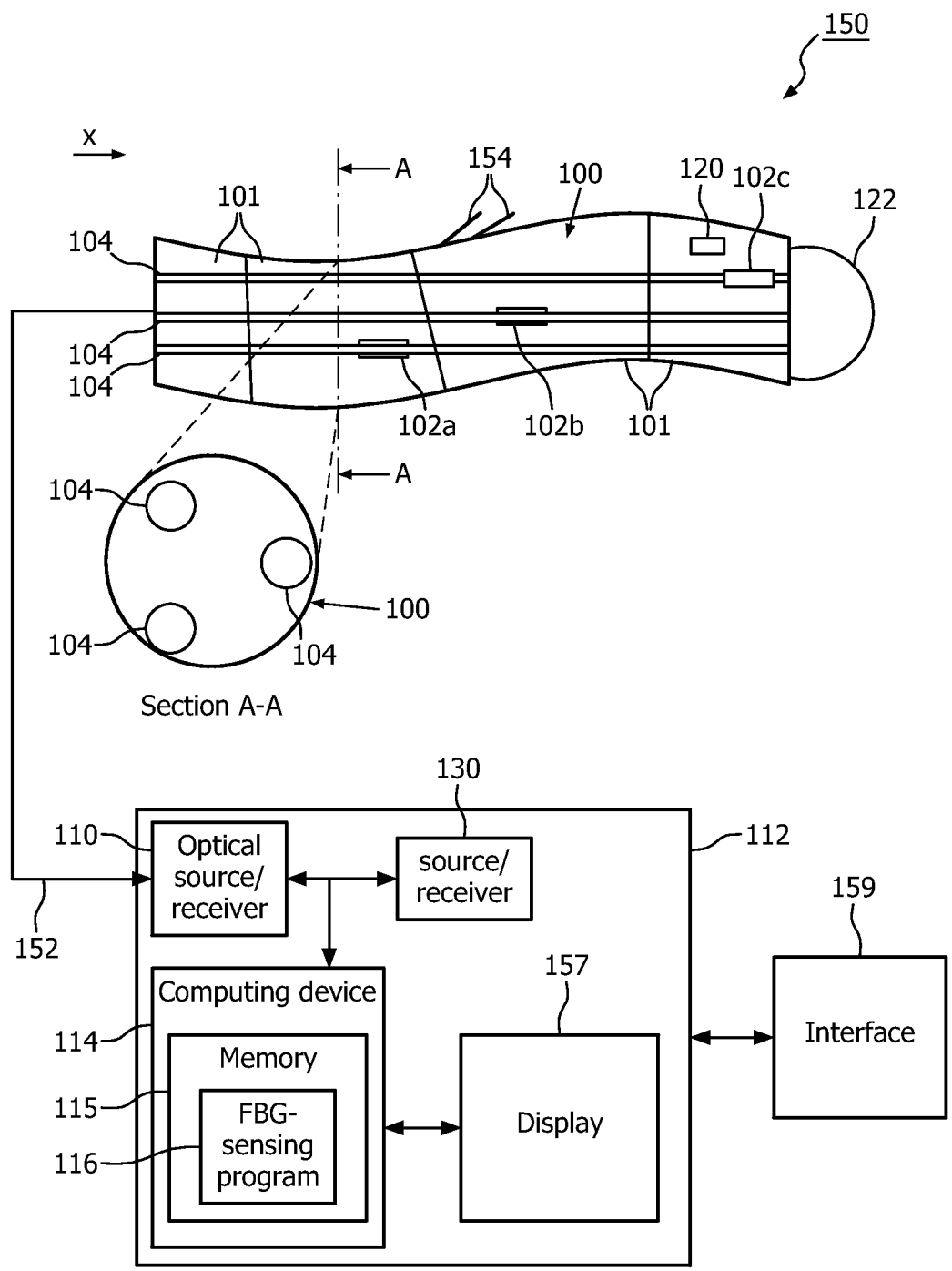
FIG. 1 is a block diagram showing an illustrative system for performing an interventional procedure in accordance with the present principles.

In many interventional procedures employing the use of guide wires or catheters, there is a need for compact and robust multipoint or distributed sensing of physiological motion characteristics and parameters including temperature, pressure, voltage changes, etc. In accordance with the present principles, Fiber-optic Bragg Gratings (FBG) can be incorporated directly into the body of an elongated instrument such as a guide wire or catheter without significantly changing the instrument mechanical properties, form factor or footprint. In addition, rapid multipoint and multiparameter measurements of segmental motion, voltage, temperature, and pressure are possible with the introduction of coatings or crystal materials (e.g., $Bi_{12}TiO_{20}$ crystals for voltage sensing, Ni—Mn—Ga memory shape metal alloys for magnetic sensing, Zn metal vapor deposition for enhanced temperature sensing, etc).

A FBG functionalized medical device such as a guide wire, catheter, or other flexible elongated instrument is described that performs simultaneous measurements of motion, voltage, temperature, pressure or other parameters in a distributed fashion such as at an "effector" segment or other segment of the instrument, e.g., the distal 10 cm segment including the tip of a loop/lasso mapping catheter used in electrophysiology procedures. Segmental motion tracking may be performed along the length of the instrument and therefore motion compensation/gating of instrument imaging data or voltage/temperature/pressure measurements may be made more accurate. Tracking deformation of the "effector" segment of the instrument may be employed to measure a change in biological tissue response to the intervention, e.g., monitoring tissue-induced FBG strains in a loop catheter to estimate electromechanical synchrony or to estimate intervention impact on cardiac contractility.

It should be understood that the present invention will be described in terms of medical instruments; however, the teachings of the present invention are much broader and are applicable to any instruments employed in tracking or analyzing complex biological or mechanical systems. It should also be understood that the illustrative example of the optical device may also include electronic components, depending on the application. The elements depicted in the FIGS. may be implemented in various combinations of hardware and provide functions which may be combined in a single element or multiple elements.

The functions of the various elements shown in the figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), and non-volatile storage.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams, state transition diagrams, pseudocode, and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable medium providing program code for use by or in connection with a computer or any instruction execution system. For the purposes of this description, a computer-usable or computer readable medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Referring now to the drawings in which like numerals represent the same or similar elements and initially to FIG. 1, an optically functionalized medical device 100 is illustratively shown in accordance with one embodiment. Device 100 may include a guide wire, catheter, or other flexible elongated instrument that permits any or all of simultaneous measurements, segmental motion tracking and/or tracking deformation.

Simultaneous measurements may be made using device 100 for motion, voltage, temperature, pressure, color, strain, magnetism, position, biochemical state, etc. in a distributed fashion. For example, multiple measurements may be made at an effector segment or any segment 101 of an instrument. The effector segment may include a distal end segment including a tip of a loop/lasso mapping catheter used in electrophysiology procedures, and more particularly, a distal end 10 cm segment. Device 100 is also capable of segmental motion tracking along the length of the instrument itself. Therefore, FBG-derived compensation and correction of instrument imaging data or voltage/temperature/pressure measurements can be made at one or more segments 101. The device 100 may also track deformation of the effector segment of the instrument to measure a change in biological tissue responsive to an intervention procedure, e.g., monitoring tissue-induced FBG strains in a loop catheter to estimate electromechanical synchrony or to estimate intervention impact on cardiac contractility. In this way, deflection experienced by device 100 may be correlated to deformations of tissue surrounding the device 100.

The device 100 includes strain or other sensors 102 which are disposed over an elongated section of the device 100. One sensor 102 may be provided in each of three fibers 104 to form a sensor triplet at a given cross-section or axial location (x-direction) in this embodiment. Other numbers of fibers may also be employed. The device 100 is preferably an elongated medical instrument for diagnosis, intervention, or therapy monitoring and may take the form of a catheter, guidewire, endoscope, etc. (with manual or automatic steering control for device navigation). The fibers 104 are introduced into the body of the instrument 100 with a series of fiber Bragg gratings or other sensors 102 spatially distributed along its length and/or clustered in functional regions of the instrument, e.g., a distal segment including a tip. The sensors 102 may form an array to collect data over a region. Each fiber 104 may include one or more sensors 102.

The sensors 102 may include uncoated FBGs for shape sensing, FBGs incorporating materials for temperature sensing (e.g. Zn metal vapor deposition), FBGs incorporating materials for voltage/magnetic field sensing (e.g. $Bi_{12}TiO_{20}$, Ni—Mn—Ga), and/or other FBGs incorporating materials for sensitivity to other biophysical parameters of interest (e.g., pH sensing, $pCO_2$, etc.). Other optical or electronic sensors may also be employed.

Device 100 may include an optical module 110 for sense fiber illumination and receiving fiber signals. The source of module 110 may be at a proximate end portion of the device and carry light using a waveguide or at the distal end portion for direct illumination. The module 110 includes a receiver function.

Device 100 may be implemented as part of a system 150 of components. An optical interrogation console 112 may be employed for readout of multiplexed signals returning from FBGs in all fibers. A computing device 114 may include a real-time FBG sensing program 116 for sensing fiber shape, mapping temperature-sensitive FBG wavelength shifts into temperature changes, mapping voltage/magnetic field sensitive FBG wavelength shifts into voltage/magnetic field characteristics, and/or mapping other custom FBG wavelength shifts into corresponding biophysical parameter measurements. The console 112 is configured for real-time interaction and visual display of instrument location and spatially distributed measurements (e.g., FBG-derived biophysical measurements, endoscope-based video or other imaging data, catheter-based video or other imaging data).

The device 100 may optionally include low-cost conventional sensors 120, e.g., electrodes for voltage sensing or may include a stabilizing/fixation mechanism 122 for holding a point on the sensing fiber fixed against a reference location of interest (e.g. a balloon with or without perforations to allow for flow past the fixation point).

The system 150 may optionally include a medical imaging system 130 to provide a more global visualization of the anatomy of interest and interventional field-of-view (e.g., CV-X-ray system for cardiac procedures, or ultrasound system for body interventions, etc.). The instrument 100 may be employed in conjunction with imaging data acquired either pre-procedurally, intra-procedurally, or simultaneously with optical interrogation. Imaging and optical data recordings can be used in combination to improve the estimates of biophysical parameters, instrument characteristics, and tissue properties to make decisions about interventional procedure guidance and monitor therapy progress.

System 150 includes a data connection 152 to/from a sensor output (or FBG interrogation output) from sensors 102a-c providing a read-out of fiber shape/additional biophysical parameters. The instrument data acquired may be carried on connection 152, e.g., real-time video (e.g., from a video endoscope), real-time ultrasound (e.g., from an intracardiac echo, ICE catheter). An instrument therapy mechanism 154 delivers, e.g., RF power for an RF ablation catheter, ultrasound (US) power delivery for a HIFU instrument, etc. The data connection 152 between the FBG-enabled instrument 100 also provide information to/from the medical imaging system 130. Feedback and control signals may be exchanged through connection 152. For example, instrument navigation may be employed as feedback based on FBG interrogation to assist in guiding the instrument 100. In addition, feedback or control signals may be employed for instrument therapy delivery based on FBG interrogation.

System 150 may include multiple processing or computing devices 114 for generating control signals, performing computations, generating video images, interpreting feedback, etc. For example, processing of distributed FBG shape measurements permits segment dependent respiratory, cardiac, or gross patient motion gating, correction of instruments, medical imaging system data, etc. In particularly useful embodiments, from one segment 101 of a sensing fiber, cardiac motion may dominate at sensor 102c, in yet another segment 101, respiratory motion may dominate at sensor 102b, whereas a third segment 101 reflects gross patient motion at sensor 102a. Multiple fibers (or even a single fiber) permit feedback from all three segments. A user, such as a surgeon or technician, can select specific segments from which to extract gating signals via graphical interaction on an instrument console 112 of system 150. The signals from these regions can then be used to gate or motion correct the actual measurements of interest to obtain motion-compensation video from a video endoscope, or motion-compensated ultrasound from an ICE catheter, or motion-corrected fluoroscopy from an X-ray imaging system, etc. In addition, processing of FBG shape measurements may be performed by processor 114 to track deformation of the "effector" segment of the instrument 100 and so monitor a change resulting from intervention, e.g., monitoring tissue-induced FBG strains in a loop catheter to estimate electromechanical synchrony or to estimate intervention impact on cardiac contractility.

The user may store data in memory 115. Memory may include programs (e.g., program 116). The program 116 may be adapted to take measurements and control sensors (e.g., FBGs). A display 157 may be provided for visualizing procedures and/or for interfacing with the console 112 and device 100 during a procedure. The user may employ a user interface 159 to interact with the console 112 and/or the instrument 100. The interface 159 may include a keyboard, a mouse, a touch screen system, etc.

Figure 2:
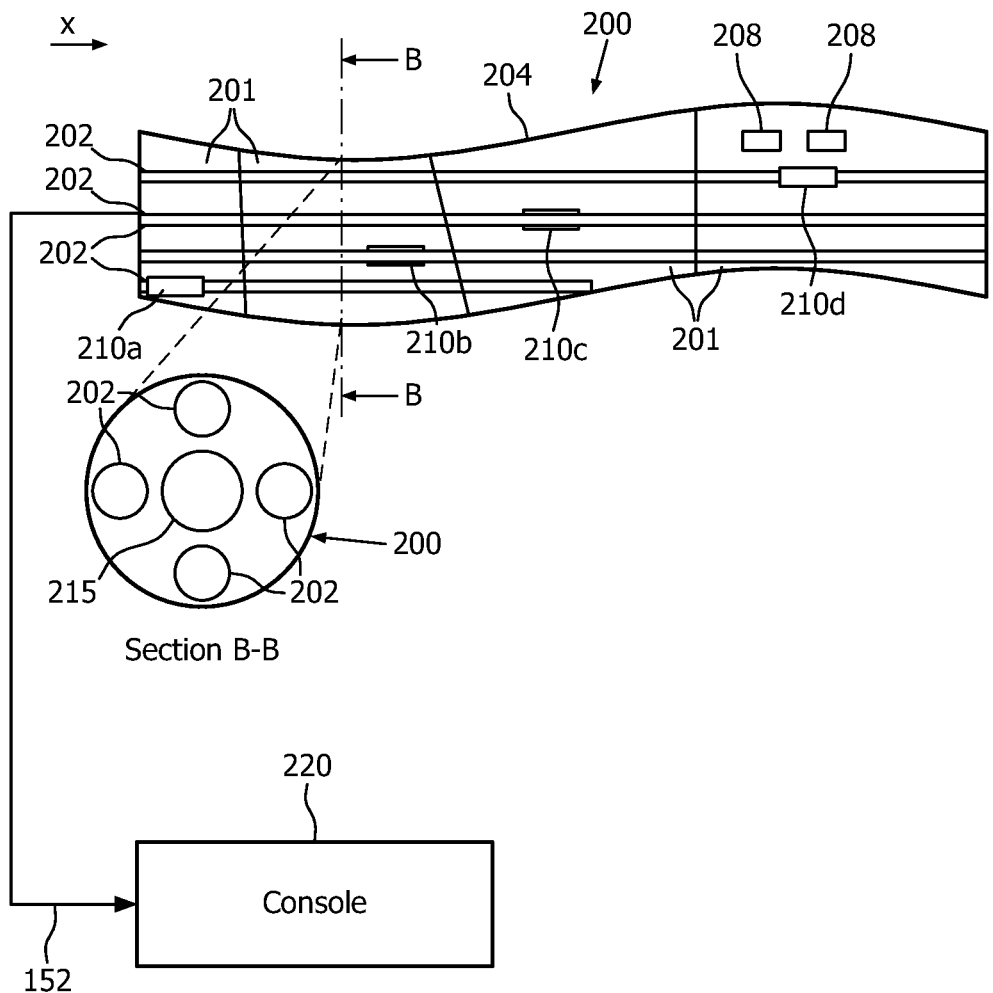
FIG. 2 is a block diagram showing an interventional instrument having sensing optical fibers and a parameter measuring fiber in accordance with the present principles.

Referring to FIG. 2, an illustrative interventional medical device 200 includes a shape sensing fiber(s) 202 in an elongated medical instrument 204 with segment specific motion correction for individual segments 201 or the device 200 as a whole. In this embodiment, the elongated instrument 204 may include low-cost sensors 208 such as electrodes for voltage mapping, miniature thermistors for temperature sensing, etc. In addition, the sensing fibers 202 include a distribution of FBGs 210a-c embedded within the instrument body. During a procedure, FBG-derived shape/motion data are visualized on a graphical display (157, FIG. 1) with instrument location shown as a registered overlay on top of pre-procedurally acquired imaging data or intra-procedurally acquired imaging data from a medical imaging system sharing a data connection with the FBG-enabled instrument. A clinician is enabled to graphically select the segments or sub-segments of the instrument 200 to be used for separate respiratory motion gating (and/or compensation) 210a, cardiac motion gating (and/or compensation) 210b, gastro-intestinal (GI) motion (and/or compensation) 210c, and gross patient motion (and/or compensation) 210d, for example. The sensor positions and locations can be predetermined or adjusted to provide spatially specific measurements concurrently from different information sources.

A workstation or console 220 takes the prescribed motion/gating signals from each of the segments or sub-segments, then computes and displays, in real-time, the motion corrected measurements of interest, e.g., gated/motion-corrected voltage measurements from an EP mapping catheter. Position tracking provided by the embedded sensing fiber 202 permits for spatial mapping and multidimensional reconstruction of data acquired by the instrument 200, e.g., video/image mapping/surface reconstruction in 3D, voltage/temperature mapping in 3D, etc. Furthermore, deformation measurements from the sensing fiber 202 can be combined with conventional instrument measurements (208) to monitor responses to the intervention. For example, a shape-sensing-enabled flexible loop catheter with conventional electrodes (208) for both voltage measurement and delivery of ablation energy can be positioned in contact with the ventricular wall during ablation and voltage measurement. Changes in deformation of the loop segment in contact with wall will reflect changes in synchrony and magnitude of myocardial motion, which is of clinical relevance in assessing response.

The workstation or console 220 can also take the position/motion signals from each of the segments or sub-segment to display, in real-time, a fused overlay of the FBG-enabled interventional device with imaging data acquired concurrently or pre-procedurally. This allows for visualization of the interventional device via FBG enabled position sensing which is especially useful for imaging modalities that do not permit direct visualization of the device itself. For example, standard catheters are poorly visible under ultrasound imaging or are completely invisible under magnetic resonance imaging. The use of FBG-enabled instrumentation in combination with imaging would facilitate intervention guidance since the imaging modality would provide feedback about tissue/organ properties whereas FBG sensing would provide information about instrument properties.

It should be understood that the instruments described herein may have many functional features and variations. For example, the instruments (100, 200, etc.) may include a working channel or lumen 215 to provide a way to by-pass fluids, to apply suction, to permit the movement of other tools and instruments, etc.

Figure 3:
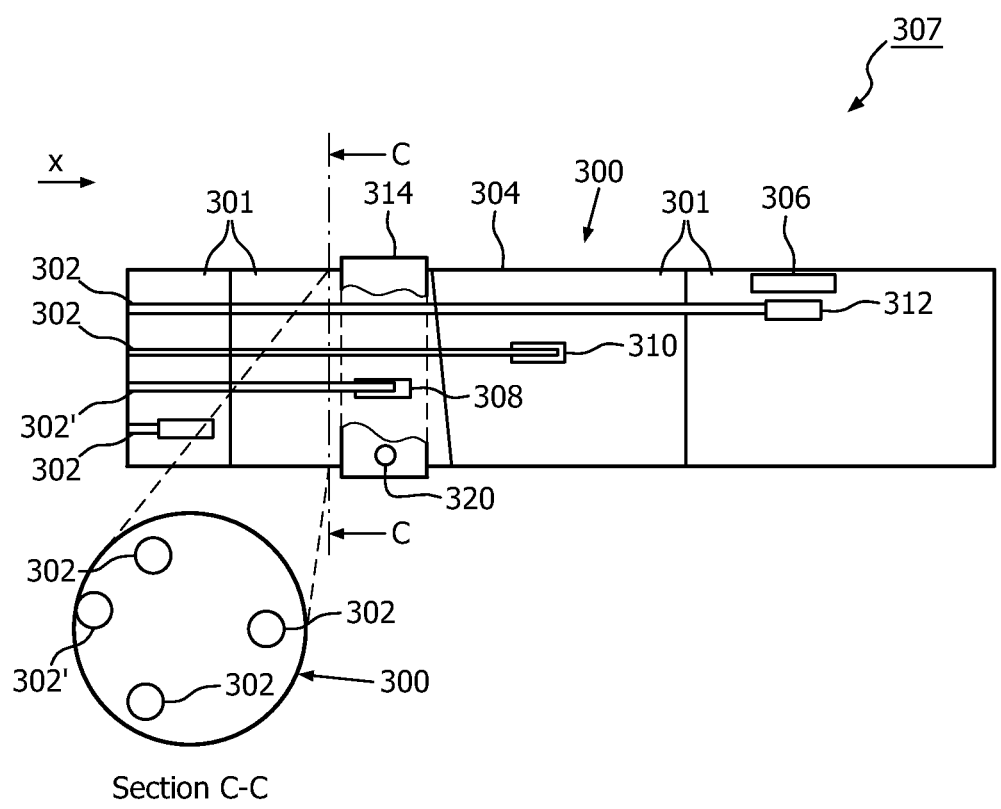
FIG. 3 is a block diagram showing an interventional instrument having sensing optical fibers and a parameter measuring fiber with windows opened to the external environment in accordance with the present principles.

Referring to FIG. 3, an illustrative interventional medical device 300 includes one or more shape sensing fibers 302 each with a single biophysical parameter sensing core and a contact/window 306 to an external environment 307. The elongated instrument 304 has FBG-based sensors for measurement of temperature, voltage, magnetic field, chemical concentration, etc. to achieve further miniaturization potential. For the measurement of scalar fields such as temperature or voltage, a single optical fiber with a distribution of FBGs spaced along the length of interest (depending on the application) is employed. For multiparameter sensing in the illustrative example, the coatings used for consecutive FBGs can be interleaved so that a temperature sensitive FBG 308 is positioned beside a voltage sensitive FBG 310, followed by a pressure sensitive FBG 312 in an alternating pattern. The pattern and distribution/spacing of these FBGs can be varied according to the instrument type and application.

Given the close proximity of each of these FBG types and a sensor of the additional shape sensing fiber 302 embedded within the instrument 300, it is also possible to apply the measured strains from the shape sensing fibers to obtain deformation-corrected temperature, pressure, or voltage measurements. The measured biophysical parameters such as temperature are used to obtain corrected estimates for fiber shape (since wavelength shifts in FBGs are strain as well as temperature sensitive). In this way, accurate and relevant multiparameter measurements can be made to adjust and further provide information during an interventional procedure.

To ensure that the biophysical parameter FBGs are able to sense environmental conditions, an embodiment in which the biophysical parameter sensing fiber 302' is eccentrically positioned close to the outer perimeter of the instrument 300 is shown. For temperature or voltage sensitized FBGs, a metallic or conductive ring 314 is placed around the instrument 300 in contact with both the FBG temperature sensor 308 and the external environment to ensure coupling. For pressure-sensitized FBGs 310, windows 306 or 320 in the outer perimeter of the instrument at or near a location of FBGs may be employed for exposure of the FBG sensor(s)

to pressure conditions in the external environment (these windows 306 or 320 can either be open or thin-membrane covered holes). These windows 306 or 320 may be closable and controlled by an operator as needed.

Figure 4A:
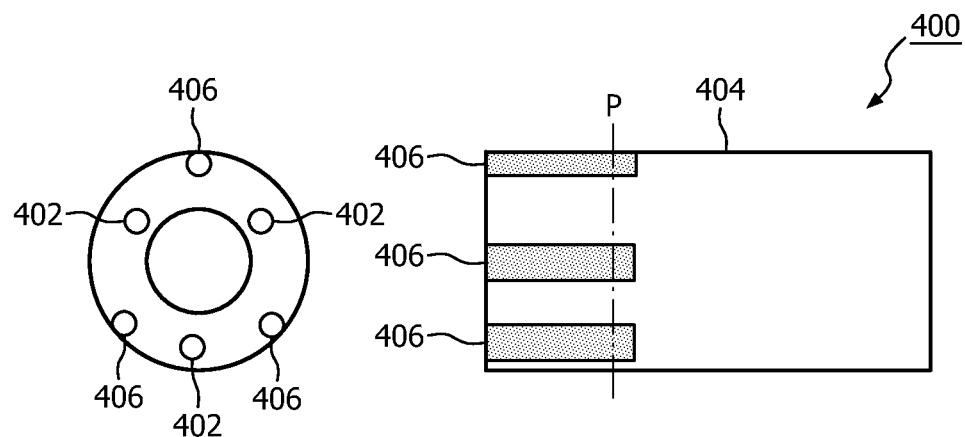
FIG. 4A is a diagram showing fiber sensors aligned to measure a parameter at a same location in accordance with the present principles.
Figure 4B:
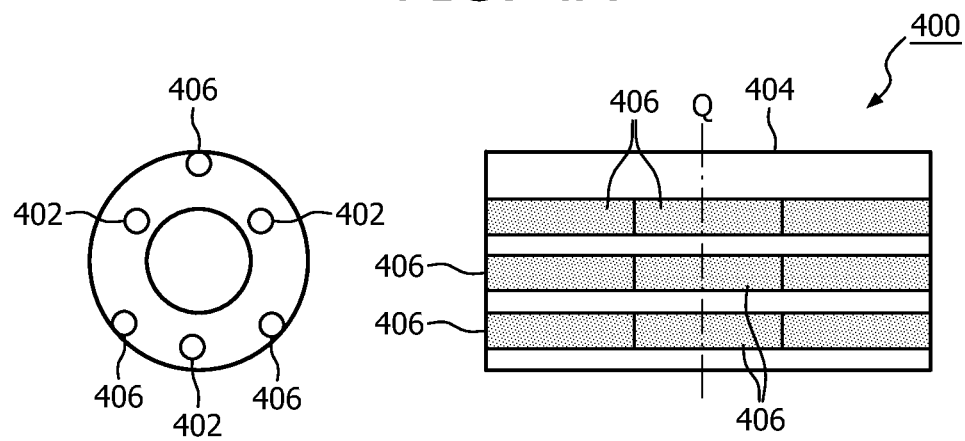
FIG. 4B is a diagram showing fiber sensors staggered to measure several parameters at a same location in accordance with the present principles.

Referring to FIGS. 4A and 4B, an illustrative interventional medical device 400 is shown in cross-section on the left and with an illustrative side diagram on the right to demonstrate the present concepts. The device 400 includes shape sensing fibers 402 in an elongated medical instrument 404 with multiple biophysical parameter sensing cores or sensors 406 which may include contacts or windows to an external environment to make measurements thereof. Aligned multiparameter sensing cores are depicted in FIG. 4A, while FIG. 4B shows staggered multiparameter sensing cores or sensors.

Multi-core arrangements of biophysical parameter sensing fibers or sensors 406 can be positioned around the shape sensing fibers 402 to permit for parameter sensing at multiple points around the instrument periphery. If the FBGs in these cores are aligned (as in FIG. 4A) so that each FBG at the same axial section (at position P) senses the same biophysical parameter, e.g. temperature, the measurements can be averaged to obtain higher signal to noise (SNR) performance.

Alternatively, the cores or sensors 406 can be staggered (as depicted in FIG. 4B) so that at the same axial contact point (Q), each of the FBGs senses a different biophysical parameter, allowing for multi-parameter sensing at the same location along the instrument 400. As in FIGS. 1-3, these multi-parameter measurements can be used jointly to derive more accurate temperature, strain, etc. corrected estimates. It should be understood that many variations of the described embodiments may exist. Different features and different parameters may be configured for a given procedure or application. In some embodiments, the elongated instrument may be reconfigurable to permit customization of the positioning of FBG sensors or even the fiber density or position relative the periphery or other feature of the instrument. It should also be understood that optical fibers may be replaced with other signals carrying devices and that optical sensors may include non-optical sensors.

Figure 5:
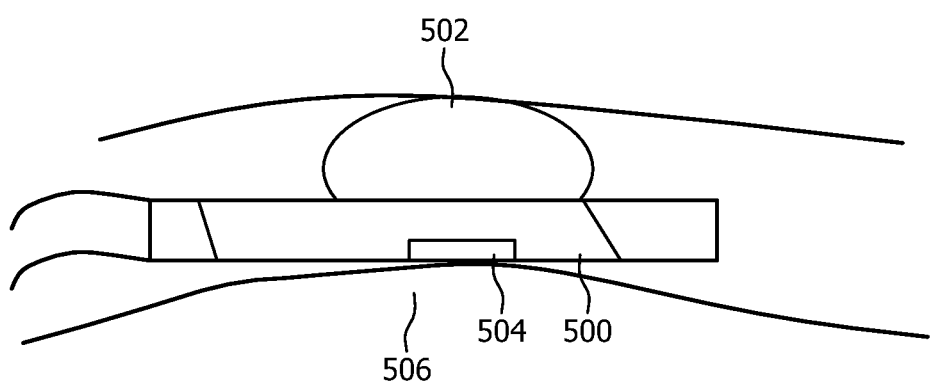
FIG. 5 is a diagram showing a stabilization device employed with optical sensors in accordance with one illustrative application.

Referring to FIG. 5, additional mechanisms or features may be employed to customize or increase the functionality of the instruments in accordance with the present principles. Any of the described embodiments may be employed together with a stabilization/mechanical fixation device 502 (e.g., based on balloons or other mechanical structures) for an instrument 500 (similar to those described as instruments 100, 200, 300) to obtain a reference location for measurements. For example, balloon deployment may be employed to fix a temperature-sensitive FBG 504 at an anatomical location 506 desired for reference temperature measurements far from a site of ablation therapy.

Another mechanism that may be employed using FBGs includes a feedback mechanism employed for feedback or control of navigation or therapy delivery based on multi-sensor distributed measurements (e.g., a temperature reference at a fixed point distant from an ablation site for monitoring and control of temperature elevation following energy delivery). The information collected at the site is employed to provide information to the technician or surgeon to provide feedback on events occurring at the site (e.g., 506). The system 150 depicted in FIG. 1, e.g., may be employed for collecting and using the feedback during a procedure.

For example, sensors (optical or non-optical) are preferably distributed such that deformation, vibration, or any other distortion mode induced in a segment of the instrument is measured to determine either a tissue response to the instrument during an interventional procedure, or feedback from the instrument about tissue-instrument interaction (e.g., haptic feedback during instrument navigation within a lumen).

Figure 6:
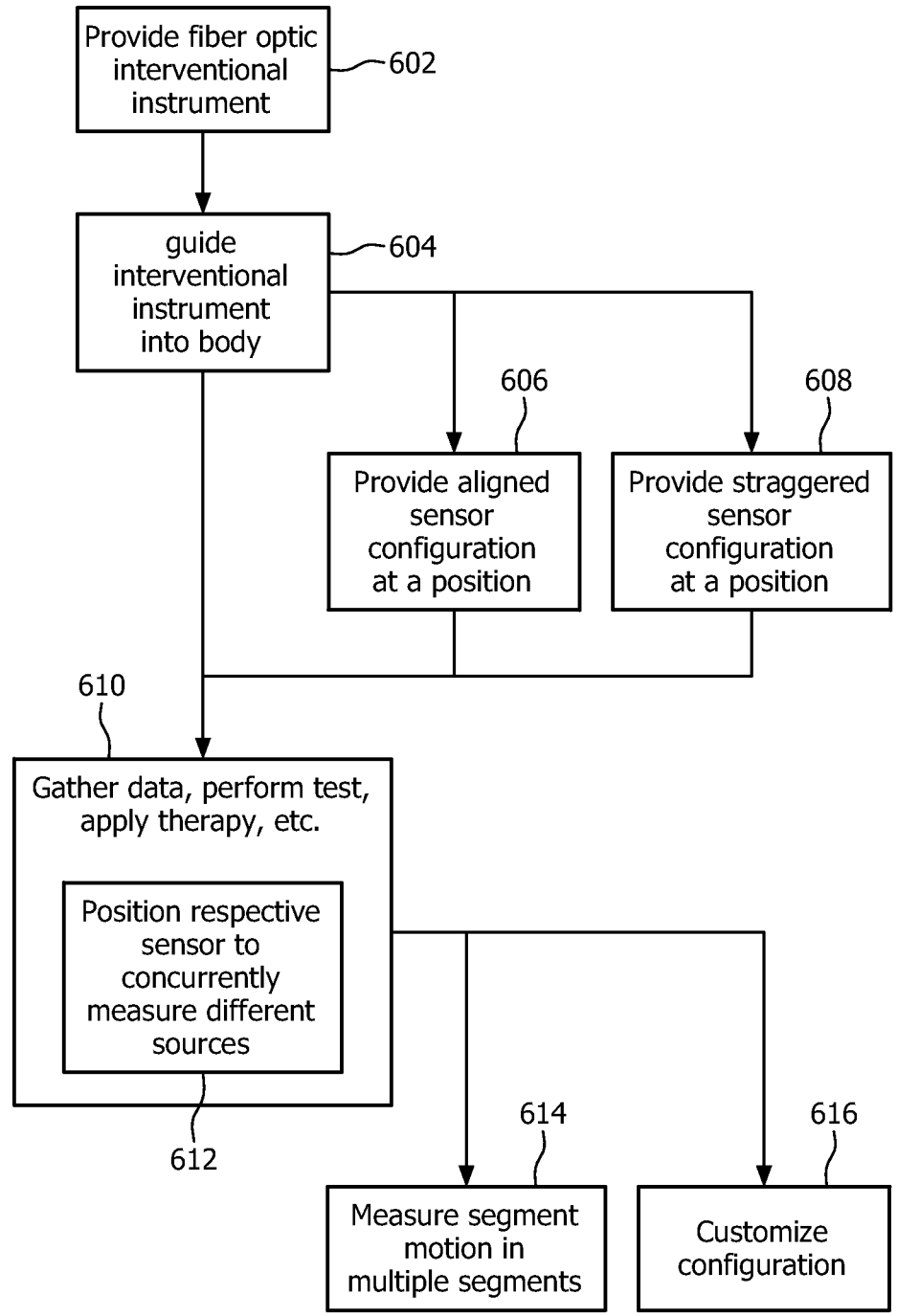
FIG. 6 is a flow diagram showing an illustrative interventional procedure in accordance with the present principles.

Referring to FIG. 6, a medical interventional method or procedure is illustratively depicted. In block 602, an interventional instrument is provided including an elongated flexible member having one or more sections, which may be segmented and disposed longitudinally. At least one optical fiber is disposed internally in the flexible member, and a plurality of optical sensors are coupled to the at least one optical fiber and distributed along a length of the flexible member such that the optical sensors are positioned to monitor separate parameters simultaneously along the flexible member to provide distributed sensing. In block 604, the interventional instrument is guided into a body to perform a medical procedure. In block 606, in one optional embodiment, a set of optical sensors associated with a plurality of optical fibers is aligned where an aligned set includes a sensor associated with each fiber such that the aligned set measures a same parameter at a same axial position along a length of the flexible member. In block 608, in another optional embodiment, a set of optical sensors associated with the plurality of optical fibers is staggered where a staggered set includes a sensor associated with each fiber such that the staggered set measures different parameters at a same axial position along a length of the flexible member.

An array of sensors may be employed to map, monitor, apply therapy, etc. to a given area. In block 610, data is concurrently gathered from a plurality of data sources by respective sensors. Testing or therapy is performed, or any other action is performed using the fiber optic interventional instrument. In one embodiment, respective sensors are positioned relatively, the relative position being determined to provide proximity to different data sources when the flexible member is located in a data gathering position in block 612.

In block 614, segmental motion of two or more of the segments is measured to provide a more accurate positional orientation for the instrument. In another embodiment, deformation of a segment of the instrument is measured using distributed sensors to determine a tissue response to the instrument during an interventional procedure. In block 616, fibers and sensor arrays may be customized and repositioned to provide a flexible design to accommodate a given procedure.

The present principles provide systems and methods for performing clinical, surgical or testing applications using fiber optic technology in medical instrumentation. Clinical applications include, but are not limited to catheter-based navigation, mapping, and ablation for treatment of atrial fibrillation or ventricular arrhythmias (FBG-functionalized ablation catheter, pulmonary vein loop catheter, coronary sinus catheter, etc.), pulmonary venous contraction monitoring, cardiac resynchronization therapy and cardiac contractility/electromechanical synchrony assessment, cardiac filter device or balloon deployment, transcatheter valve replacement, and FBG-enabled endoscopy-based procedures (imaging, biopsy, ablation, NOTES, etc.) in cardiac, pulmonary, or body interventions. Other applications and procedures where the present principles are applicable also exist and are contemplated by the present embodiments.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods for optical sensing—enabled interventional instruments for rapid distributed measurements of biophysical parameters (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An interventional instrument, comprising:
   an elongated flexible member having one or more sections disposed longitudinally;
   at least one optical fiber disposed internally in the flexible member;
   a plurality of uncoated optical sensors coupled to the at least one optical fiber and distributed along a length of the flexible member to monitor a shape of the interventional instrument; and
   a plurality of coated and/or crystalized optical sensors coupled to the at least one optical fiber and distributed along a length of the flexible member such that the coated and/or crystalized optical sensors are positioned to monitor a plurality of different biophysical parameters simultaneously at at least one of different positions and for different data sources along the flexible member to provide distributed sensing, wherein each coated and/or crystalized optical sensor incorporates at least one of a coating material and a crystal material.

2. The interventional instrument as recited in claim 1, wherein the elongated flexible member includes one of a guide wire, a catheter and an endoscopic tool.

3. The interventional instrument as recited in claim 1, wherein the at least one optical fiber includes a plurality of optical fibers distributed within the flexible member.

4. The interventional instrument as recited in claim 3, wherein the plurality of coated and/or crystalized optical sensors include an aligned set of coated and/or crystalized optical sensors associated with the plurality of optical fibers where the aligned set includes a coated and/or crystalized optical sensor associated with each fiber such that the aligned set measures a same biophysical parameter at a same axial position along a length of the flexible member.

5. The interventional instrument as recited in claim 3, wherein the plurality of coated and/or crystalized optical sensors include a staggered set of coated and/or crystalized optical sensors associated with the plurality of optical fibers where the staggered set includes a coated and/or crystalized optical sensor associated with each fiber such that the staggered set measures different biophysical parameters at a same axial position along a length of the flexible member.

6. The interventional instrument as recited in claim 1, wherein the interventional instrument is employed in conjunction with imaging data acquired pre-procedurally, intra-procedurally, or simultaneously with optical interrogation.

7. The interventional instrument as recited in claim 1, wherein the coated and/or crystalized optical sensors measure at least one of motion, strain, magnetism, voltage, temperature, pressure, biochemical state, and color.

8. The interventional instrument as recited in claim 1, wherein at least two coated and/or crystalized optical sensors have a relative position therebetween, the relative position being determined to provide proximity to different data sources when the flexible member is located in a data gathering position such that data is gathered concurrently from each data source by a respective sensor of the at least two coated and/or crystalized optical sensors.

9. The interventional instrument as recited in claim 1, wherein the one or more sections include one or more segments including the coated and/or crystalized optical sensors wherein the coated and/or crystalized optical sensors measure segmental motion of each segment.

10. The interventional instrument as recited in claim 1, wherein the coated and/or crystalized optical sensors are further distributed along the length of the flexible member such that the coated and/or crystalized optical sensors are positioned to measure at least one of a deformation, vibration, or other distortion mode induced in a segment of the interventional instrument.

11. The interventional instrument as recited in claim 1, wherein the flexible member includes a closeable aperture to expose at least one of the plurality of coated and/or crystalized optical sensors.

12. A system for an interventional procedure, comprising:
   an interventional instrument including
      an elongated flexible member having one or more segmented sections disposed longitudinally,
      at least one optical fiber disposed internally in the flexible member,
      a plurality of uncoated optical sensors coupled to the at least one optical fiber and distributed along a length of the flexible member to monitor a shape of the interventional instrument, and
      a plurality of coated and/or crystalized optical sensors coupled to the at least one optical fiber and distributed along a length of the flexible member such that the coated and/or crystalized optical sensors are positioned to monitor a plurality of different biophysical parameters simultaneously at at least one of different positions and for different data sources to provide distributed sensing, wherein each coated and/or crystalized optical sensor incorporates at least one of a coating material and a crystal material; and
   a workstation configured to provide an interface to control the interventional instrument and to perform a procedure using the interventional instrument.

13. The system as recited in claim 12, further comprising:
   a position and/or shape tracking system for tracking the interventional instrument during an interventional procedure wherein the workstation includes a display such that position data collected from the interventional instrument is overlaid on image data.

14. The system as recited in claim 12, further comprising:
   a therapy mechanism disposed on the interventional instrument and controlled using the workstation such that therapy is applied to tissue during an interventional procedure.

15. The system as recited in claim 12, further comprising:
a fixation mechanism disposed on the interventional instrument and controlled using the workstation such that activation of the fixation mechanism stabilizes or positions at least one of the optical sensors relative to a target location during an interventional procedure.

16. The system as recited in claim 12,
wherein the at least one optical fiber includes a plurality of optical fibers distributed within the flexible member, and
wherein the plurality of coated and/or crystalized optical sensors include an aligned set of coated and/or crystalized optical sensors associated with the plurality of optical fibers where the aligned set includes a coated and/or crystalized optical sensor associated with each fiber such that the aligned set measures a same biophysical parameter at a same axial position along a length of the flexible member.

17. The system as recited in claim 12,
wherein the at least one optical fiber includes a plurality of optical fibers distributed within the flexible member and
wherein the plurality of coated and/or crystalized optical sensors include a staggered set of coated and/or crystalized optical sensors associated with the plurality of optical fibers where the staggered set includes a coated and/or crystalized optical sensor associated with each fiber such that the staggered set measures different biophysical parameters at a same axial positions along a length of the flexible member.

18. The system as recited in claim 12, wherein at least two coated and/or crystalized optical sensors have a relative position therebetween, the relative position being determined to provide proximity to different data sources when the flexible member is located in a data gathering position such that data is gathered concurrently from each data source by a respective sensor of the at least two coated and/or crystalized optical sensors.

19. The system as recited in claim 12, wherein the one or more segments include a plurality of segments including at least one of the uncoated optical sensors and the coated and/or crystalized optical sensors wherein the at least one of the uncoated optical sensors and the coated and/or crystalized optical sensors measure segmental motion of each segment.

20. The system as recited in claim 12,
wherein at least one of the uncoated optical sensors and the coated and/or crystalized optical sensors are distributed along the length of the flexible member such that the at least one of the uncoated optical sensor and the coated and/or crystalized optical sensors are positioned to measure a deformation of a segment of the interventional instrument; and
wherein the workstation is further configured to determine a tissue response to the interventional instrument during the procedure based on the measured deformation of the segment of the interventional instrument.

21. The system as recited in claim 12, wherein the flexible member includes a closeable aperture to expose at least one of the plurality of coated and/or crystalized optical sensors.

22. The system as recited in claim 12, wherein the interventional instrument is employed in conjunction with imaging data acquired pre-procedurally, intra-procedurally, or simultaneously with optical interrogation.

23. A medical interventional method, comprising:
providing an interventional instrument including
an elongated flexible member having one or more sections disposed longitudinally,
at least one optical fiber disposed internally in the flexible member,
a plurality of uncoated optical sensors coupled to the at least one optical fiber and distributed along a length of the flexible member to monitor a shape of the interventional instrument, and
a plurality of coated and/or crystalized optical sensors coupled to the at least one optical fiber and distributed along a length of the flexible member such that the coated and/or crystalized optical sensors are positioned to monitor a plurality of different biophysical parameters simultaneously at at least one of different positions and for different data sources along the flexible member to provide distributed sensing, wherein each coated and/or crystalized optical sensor incorporates at least one of a coating material and a crystal material; and
guiding the interventional instrument into a body to perform an interventional procedure.

24. The medical interventional method as recited in claim 23, wherein the plurality of coated and/or crystalized optical sensors include an aligned set of coated and/or crystalized optical sensors associated with a plurality of optical fibers wherein at least one coated and/or crystalized optical sensor is associated with each optical fiber at a substantially same axial position along a length of the flexible member such that the optical sensors in the aligned set measure a same biophysical parameter.

25. The medical interventional method as recited in claim 23, wherein the plurality of coated and/or crystalized optical sensors include a staggered set of optical sensors associated with the plurality of optical fibers wherein at least one coated and/or crystalized optical sensor is associated with each optical fiber at a substantially same axial position along a length of the flexible member such that the optical sensors in the staggered set measure different biophysical parameters.

26. The medical interventional method as recited in claim 23, further comprising:
gathering data concurrently from a plurality of data sources by respective coated and/or crystalized optical sensors wherein the respective coated and/or crystalized optical sensors have a relative position therebetween, the relative position being determined to provide proximity to different data sources when the flexible member is located in a data gathering position.

27. The medical interventional method as recited in claim 23, further comprising:
measuring segmental motion of two or more segments of the one or more sections.

28. The medical interventional method as recited in claim 23, further comprising:
measuring deformation of a segment of the interventional instrument using at least one of the uncoated optical sensors and the coated and/or crystalized optical sensors; and
determining a tissue response to the interventional instrument during the interventional procedure based on the measured deformation of the segment of the interventional instrument.

* * * * *